United States Patent
Hope et al.

(10) Patent No.: US 7,309,805 B2
(45) Date of Patent: Dec. 18, 2007

(54) METHOD AND SYSTEM TO CONTACT AN IONIC LIQUID CATALYST WITH OXYGEN TO IMPROVE A CHEMICAL REACTION

(75) Inventors: Kenneth D. Hope, Kingwood, TX (US); Donald A. Stern, Kingwood, TX (US); Elizabeth A. Benham, Spring, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 85 days.

(21) Appl. No.: 10/978,547

(22) Filed: Nov. 1, 2004

(65) Prior Publication Data

US 2006/0020088 A1 Jan. 26, 2006

Related U.S. Application Data

(60) Provisional application No. 60/516,516, filed on Oct. 31, 2003.

(51) Int. Cl.
*C07C 2/04* (2006.01)

(52) U.S. Cl. ............... 585/502; 585/518; 526/171; 526/348

(58) Field of Classification Search ........... 585/502, 585/518; 526/171, 348
See application file for complete search history.

(56) References Cited

U.S. PATENT DOCUMENTS

| | | | |
|---|---|---|---|
| 2,405,950 | A | 8/1946 | Hanford |
| 4,827,064 | A | 5/1989 | Wu |
| 5,087,782 | A | 2/1992 | Pelrine |
| 5,196,574 | A | 3/1993 | Kocal |
| 5,304,615 | A | 4/1994 | Ambler et al. |
| 5,386,072 | A | 1/1995 | Cozzi et al. |
| 5,731,101 | A | 3/1998 | Sherif et al. |
| 5,824,832 | A | 10/1998 | Sherif et al. |
| 5,891,830 | A | 4/1999 | Koltermann et al. |
| 6,087,307 | A | 7/2000 | Kaminski et al. |
| 6,107,374 | A | 8/2000 | Stevens et al. |
| 6,395,948 | B1 | 5/2002 | Hope et al. |
| 2002/0128532 | A1 | 9/2002 | Hope et al. |
| 2003/0085156 | A1 | 5/2003 | Schoonover |
| 2004/0005985 | A1 | 1/2004 | Hope et al. |
| 2004/0030075 | A1 | 2/2004 | Hope et al. |

FOREIGN PATENT DOCUMENTS

| | | |
|---|---|---|
| EP | 0791643 A1 | 8/1997 |
| WO | WO 88/06476 A1 | 9/1988 |
| WO | WO 95/21871 A1 | 8/1995 |
| WO | WO 95/21872 A1 | 8/1995 |
| WO | WO 98/50153 A1 | 11/1998 |
| WO | WO 99/38938 A1 | 8/1999 |
| WO | WO 00/32658 A1 | 6/2000 |
| WO | WO 00/41809 A1 | 7/2000 |
| WO | WO 01/64622 A2 | 9/2001 |
| WO | WO 01/64622 A3 | 9/2001 |
| WO | WO 03/089390 A2 | 10/2003 |

OTHER PUBLICATIONS

Jacobs et al., Tetrahedron. Letters 43 (2002) 8107-8110.*
Jacobs et al., Tet. Letters 43 (2002) 8107-8110.*
Wasserscheid et al, Ange. Chem. International Ed., vol. 39 Oct. 27, 2000, pp. 3772-3789.*
Hope, Kenneth D., et al., Method For Manufacturing High Viscosity Polyalphaolefins Using Ionic Liquid Catalysts, Filed—Jul. 27, 2004, U.S. Appl. No. 10/900,221, Specification & Drawings (27 pgs.).
Wasserscheid P. et al., "Ionic Liquids—New Solutions for Transition Metal Catalysis," Ange Chem. International Edition, vol. 39, Oct. 27, 2000, pp. 3772-3789.
Schubert, H., "Mechanical Emulsification—New Developments and Trends," Aiche National Meeting, Nov. 12, 2000, XP001160577, 15 pgs.

* cited by examiner

*Primary Examiner*—Robert D. Harlan
(74) *Attorney, Agent, or Firm*—Conley Rose, P.C.; Rodney B. Carroll (57) ABSTRACT

In an embodiment, a method is disclosed to increase the activity of an ionic liquid catalyst comprising contacting an ionic liquid catalyst with oxygen. In another embodiment, a method is disclosed comprising introducing into a reaction zone a monomer feed and an ionic liquid catalyst and controlling the amount of oxygen present in the reaction zone to maintain a conversion reaction of the monomer. In another embodiment, a polyalphaolefin oligomerization system is disclosed comprising a reactor configured to receive and mix monomer, ionic liquid catalyst, and oxygen; and a controller coupled to an oxygen source and configured to control the amount of oxygen present in a catalyzed reaction zone to maintain a conversion reaction of the monomer.

29 Claims, 1 Drawing Sheet

Fig. 1

METHOD AND SYSTEM TO CONTACT AN IONIC LIQUID CATALYST WITH OXYGEN TO IMPROVE A CHEMICAL REACTION

CROSS-REFERENCE TO RELATED APPLICATIONS

This application claims the benefit of and priority to provisional U.S. Patent Application No. 60/516,516, filed Oct. 31, 2003 and entitled "Method and System to Contact an Ionic Liquid Catalyst with Oxygen to Improve a Chemical Reaction." This application is related to co-pending U.S. patent application Ser. No. 10/420,26 1, filed Apr. 22, 2003, and entitled "Method for Manufacturing High Viscosity Polyalphaolefins Using Ionic Liquid Catalysts," which claims the benefit of and priority to provisional U.S. Patent Application No. 60/374,528, filed Apr. 22, 2002 and entitled "Method for Manufacturing High Viscosity Polyalphaolefins Using Ionic Liquid Catalysts." This application is also related to co-pending U.S. patent application Ser. No. 10/420,182, filed Apr. 22, 2003, and entitled "Method for Manufacturing Ionic Liquid Catalysts." This application is also related to U.S. patent application Ser. No. 10/978,792 filed on Nov. 1, 2004 and entitled "Method and System to Add High Shear to Improve an Ionic Liquid Catalyzed Chemical Reaction" which claims the benefit of and priority to provisional U.S. Patent Application No. 60/5 16,501, filed Oct. 31, 2003. Each of the above-listed applications is hereby incorporated herein by reference in its entirety for all purposes.

FIELD OF THE INVENTION

The present invention generally relates to ionic liquid catalytic systems for chemical conversions. More specifically, the invention relates to increased activity of ionic liquid catalysts for increased monomer conversion in the manufacture of polyalphaolefin products.

BACKGROUND

Ionic liquid catalysts may be used to catalyze a variety of chemical reactions, for example the oligomerization of alpha olefins to produce polyalphaolefins (PAO). A polyalphaolefin is a synthetic hydrocarbon liquid that is typically manufactured from the oligomerization of $C_6$ to $C_{20}$ alpha olefins. Polyalphaolefins are used in various industries as lubricants in gear oils, greases, engine oils, fiber optic gels, transmission oils, and various other lubricant applications. Ionic liquid catalysts used to produce PAO can be quite costly. Therefore, there is a need in the art for a method to increase the efficiency of an ionic liquid catalyst, for example to increase the ionic liquid catalyst activity and still maintain the desired conversion with a lesser amount of catalyst, thereby improving economics of a process.

SUMMARY OF THE INVENTION

In an embodiment, a method is disclosed to increase the activity of an ionic liquid catalyst comprising contacting an ionic liquid catalyst with oxygen. In another embodiment, a method is disclosed comprising introducing into a reaction zone a monomer feed and an ionic liquid catalyst and controlling the amount of oxygen present in the reaction zone to maintain a conversion reaction of the monomer. In another embodiment, an oligomerization system is disclosed comprising a reactor configured to receive and mix monomer, ionic liquid catalyst, and oxygen; and a controller coupled to an oxygen source and configured to control the amount of oxygen present in a catalyzed reaction zone to maintain a conversion reaction of the monomer.

DETAILED DESCRIPTION

The invention relates to a system and or method to contact an ionic liquid catalyst with oxygen to increase the activity of the ionic liquid catalyst within a production process. The invention also relates to a system and or method to contact an ionic liquid catalyst with water to increase the activity of the ionic liquid catalyst within a production process. Additionally, the invention relates to a system and or method to contact an ionic liquid catalyst with oxygen and water to increase the activity of the ionic liquid catalyst within a production process. Generally, the invention may be applied to any ionic liquid catalyzed reaction in which oxygen can impact the reaction rate, conversion percentage, catalyst activity, properties of the reaction product, or any combination of these factors. Contacting oxygen with an ionic liquid droplet in the manufacture of polyalphaolefins is a process that may impact one or more of these factors. In addition, in an olefin oligomerization reaction, the size of the ionic liquid droplet can impact one or more of these factors.

The invention also relates to a process to produce polyalphaolefins comprising: 1) contacting a monomer feedstock with an ionic liquid catalyst; and 2) recovering a polyalphaolefin product; wherein the ionic liquid catalyst is contacted with oxygen, water, or both. In some some embodiments of such a polyalphaolefin process, the ionic liquid catalyst is contacted with oxygen. In other embodiments, the ionic liquid catalyst is contacted with water. In yet other embodiments, the ionic liquid catalyst is contacted with oxygen and water. The monomer feedstock, ionic liquid catalyst, quantity of oxygen and/or water, and other process parameters are described herein.

The following disclosure primarily focuses on the implementation of the invention to the production of PAOs. However, it should be understood that the scope of the present invention is defined by the claims and not limited to a particular embodiment described herein. Thus, the invention described herein may be equally applied to other olefin polymerization and/or oligomerization reactions.

Figure 1:
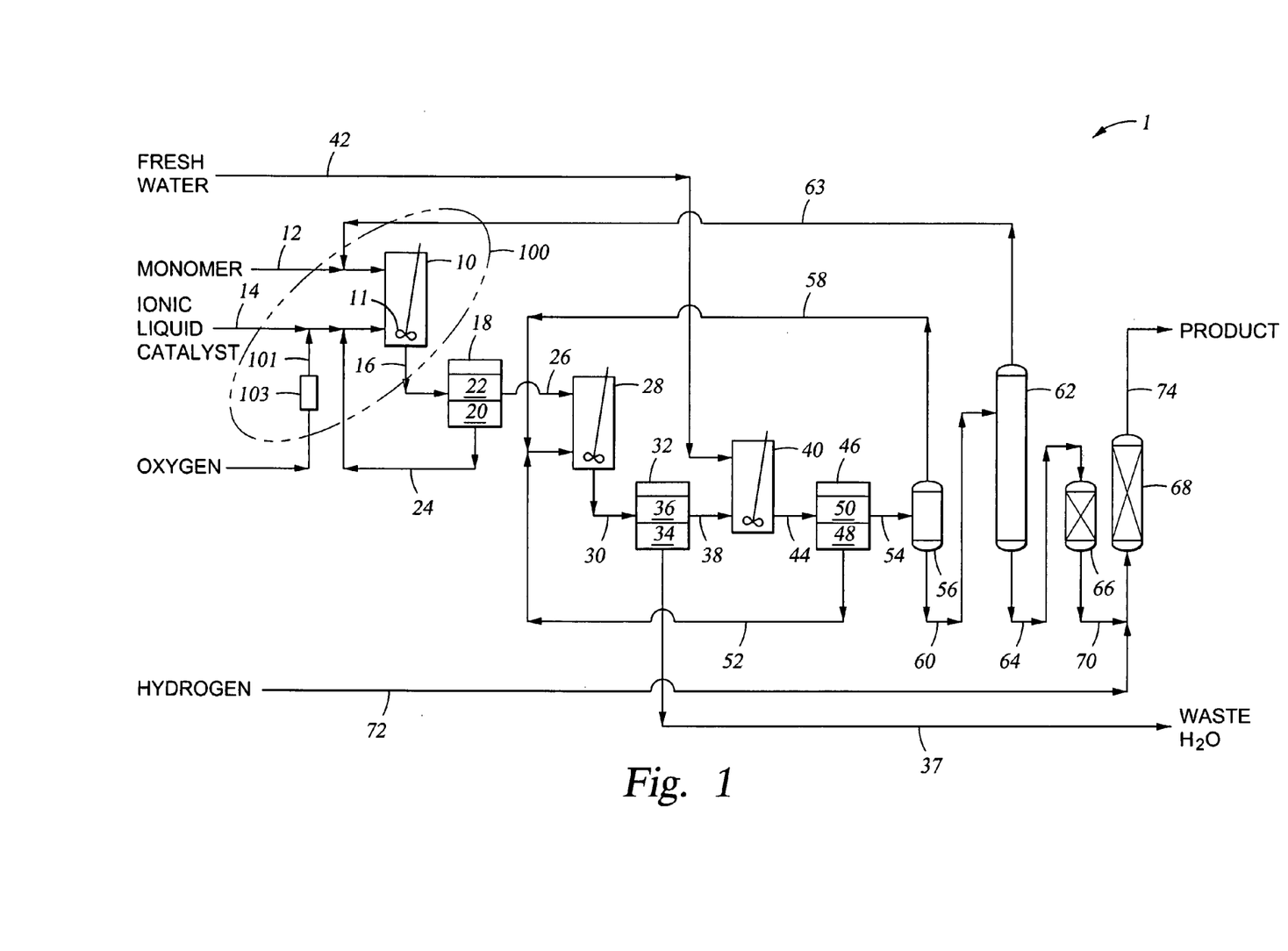
FIG. 1 is a process flow schematic of one embodiment of the system to contact an ionic liquid catalyst with oxygen incorporated within a process for manufacturing a hydrogenated polyalphaolefin product.

FIG. 1 depicts a system 100 to contact an ionic liquid catalyst with oxygen for increasing the activity of the ionic liquid catalyst within a production process 1 for manufacturing a hydrogenated polyalphaolefin (PAO) product. The system 100 comprises a reactor 10 configured to receive and mix a reactant feed, ionic liquid catalyst, and oxygen and a controller 103 coupled to an oxygen source (not shown) and configured to control the amount of oxygen present in a catalyzed reaction zone to maintain a conversion reaction of the reactant. System 100 includes the introduction of both a reactant feed via line 12 and an ionic liquid catalyst via line 14 into a reaction zone of reactor 10 and withdrawing from the reaction zone of reactor 10 via product line 16 a reaction effluent. In an embodiment, oxygen may be introduced into the system 100 by injecting oxygen into the ionic liquid catalyst line 14 via oxygen injection line 101, as shown, in an amount controlled by controller 103, to pre-contact the ionic liquid catalyst in line 14, prior to the reaction zone. Alternatively, oxygen can be injected into reactant feed line 12 (not shown) or injected directly into reactor 10 (not shown) to contact the ionic liquid catalyst with oxygen within the reaction zone. Alternatively, reactant feed and ionic liquid catalyst can be combined and fed via a single feed line (not shown) and oxygen can be injected into the combined feed line. In an embodiment, oxygen is injected into a line as described previously by adding oxygen, for example up to 5 vol. %, to the suction side of a pump located in such line, for example a high shear pump.

The reaction that occurs within the reaction zone may be an oligomerization reaction. In an embodiment, the reaction zone of system 100 comprises an oligomerization reaction in reactor 10 wherein feed stream 12 comprises a monomer of alpha-olefins and product line 16 comprises a polyalphaolefin product. Non-limiting examples of suitable alpha olefin monomers include alpha olefins having 4 to 20 carbon atoms, alternatively 6 to 20 carbon atoms, alternatively 8 to 16 carbon atoms, and alternatively 10 to 14 carbon atoms.

The following disclosure primarily focuses on a PAO production embodiment, but it should be understood that the scope of the present invention is defined by the claims and not limited to a particular embodiment described herein. For example, in an alternate embodiment, the reaction zone of system 100 comprises a general oligomerization reaction in reactor 10 wherein feed stream 12 comprises an oligomerizable olefin and product stream 16 comprises an oligomerization product. Non-limiting examples of suitable oligomerizable olefins include linear, monoolefins and mixtures thereof having greater than 3 carbon atoms. Alternatively the monoolefins have from 4 to 30 carbon atoms, and alternatively 4 to 20 carbon atoms wherein the double bond may be positioned anywhere along the linear carbon chain. Non-limiting examples of suitable olefins include 1-propene, 1-butene, 2-butene, 1-pentene, 2-pentene, and mixtures thereof.

The reaction zone of the polyalphaolefin oligomerization process can be defined by any reaction means known in the art that provides for the contacting of the monomer with the ionic liquid under suitable reaction conditions maintained and controlled so as to provide for the reaction of the monomer to thereby give the polyalphaolefin product. The reaction zone is generally defined by a reactor vessel, reactor 10, into which the monomer and ionic liquid catalyst are introduced. The monomer and ionic liquid catalyst can be introduced separately into the reaction zone via separate feed streams, the monomer via line 12 and the ionic liquid catalyst via line 14 as shown in FIG. 1, or they can be introduced together as a premixed mixture. Because the monomer feed and ionic liquid catalyst are generally immiscible fluids, the reactor 10 may be equipped with a mixing or stirring means, such as stirrer 11 in FIG. 1, for mixing the monomer feed and ionic liquid catalyst to provide intimate contact of the two fluids or to provide a substantially homogenous mixture of monomer feed and ionic liquid catalyst. One type of reactor that suitably provides for the required mixing of the monomer feed and ionic liquid catalyst is known in the art as a continuous stirred tank reactor (CSTR).

The reaction conditions within the reaction zone are maintained so as to provide suitable reaction conditions for the oligomerization of the alpha olefin monomer feed to give a polyalphaolefin product. The reaction pressure generally can be maintained in the range of from below atmospheric upwardly to about 250 psig. Since the reaction is not significantly pressure dependent, it is most economical to operate the reactor at a low pressure, for example, from about atmospheric to about 50 psig and, alternatively, from atmospheric to 25 psig. The reaction temperature is to be maintained during the reaction so as to keep the reactants and catalyst in the liquid phase. Thus, generally, the reaction temperature range is from about 20° F. to about 200° F. In an embodiment, the reaction temperature is in the range of from about 40° F. to about 150° F., and, alternatively, from 50° F. to 110° F.

The residence time of the feed within the reaction zone has a small influence on the resultant reaction product. As used herein, the term "residence time" is defined as being the ratio of the reactor volume to the volumetric introduction rate of the feeds, both the monomer feed and the ionic liquid catalyst feed, charged to or introduced into the reaction zone defined by a reactor. The residence time is in units of time. The reactor volume and feed introduction rate are such that the residence time of the total of the monomer feed and ionic liquid catalyst feed is generally in the range upwardly to about 300 minutes, but due to the need to have sufficient residence time for the reaction to take place and to economic considerations, the residence time is more appropriately in the range of from about 1 minute to about 200 minutes. In an embodiment, the residence time is in the range of from about 2 minutes to about 120 minutes and, alternatively, from 5 minutes to 60 minutes.

In some embodiments, the ionic liquid and oxygen are contacted prior to the reaction zone. In other embodiments, the ionic liquid and oxygen are contacted within the reaction zone. The amount of oxygen present in the reaction zone may be controlled by controller 103 to maintain the reaction. The amount of oxygen present in the reaction zone may be controlled by controlling the amount of oxygen in the monomer feed to the reaction zone, controlling the amount of oxygen in an ionic liquid catalyst feed to the reaction zone, controlling the amount of oxygen in a combined monomer and ionic liquid catalyst feed to the reaction zone, controlling the amount of oxygen in a gas located in a headspace above the liquid components present in the reaction zone, or combinations thereof. In an embodiment, the oxygen comprises from at least about 0.5 to about 100 wt. % of the gas in the headspace above the reaction zone, alternatively from about 0.5 to about 50 wt. %, alternatively from about 0.5 to about 21 wt. %, alternatively from about 18 to about 21 wt. %, alternatively from about 4 to about 21 wt. %, alternatively from about 0.5 to 8; alternatively from about 1 to 8; alternatively from about 3 to 8; and alternatively from about 5 to 8 weight percent. Additionally, the oxygen may be added to the system 100 in such a manner so as to maintain a constant partial pressure of oxygen in the reaction zone, thereby replacing oxygen that may be consumed in the reaction. In all embodiments, the amount of oxygen present in the reaction zone should be controlled such that the amount is considered safe, due to flammability concerns at higher concentrations.

In an embodiment, the amount of oxygen present in the reaction zone should be controlled such that the amount is sufficient to maintain the desired reaction in the reaction zone. In some embodiments, the amount of oxygen present in the reaction zone is controlled to obtain a conversion of monomer feed to equal to or greater than about 20 weight percent. In other embodiments, the amount of oxygen present in the reaction zone is controlled to obtain a conversion of monomer feed to equal to or greater than about 30, 40, 50, 60, 70, or 75 weight percent. The lower amount of oxygen for a given ionic liquid catalyst composition may be determined experimentally by iteratively reducing the amount of oxygen in the reaction zone and monitoring the monomer conversion until such conversion is unacceptable for the desired reaction. What constitutes acceptable ionic liquid catalyst activity may depend upon, for example, the specific catalyst composition, the reaction conditions, and/or the types and properties (such as viscosity targets) for the end products being made. The routine experimentation required to determine the amount of oxygen required to achieve the effects described herein for a particular catalyst composition, the reaction conditions, and/or end product combination is within the ability of those skilled in the art in light of this disclosure.

Any suitable oxygen source may be used to control the amount of oxygen present in the reaction zone, for example a gas comprising oxygen, a liquid comprising oxygen, or both. In an embodiment where the amount of oxygen present in a headspace gas is controlled, an amount of oxygen may be added by directly injecting oxygen into the headspace. In an alternate embodiment, an amount of oxygen may be added by bubbling oxygen up through the reaction zone. For example, an oxygen source may be coupled to a distribution plate in the bottom of the reactor 10 for adding oxygen into the reactor. In an embodiment, the oxygen source (not shown in FIG. 1) may be pure oxygen, air, dried air (i.e., air have a reduced amount of water), oxygen enriched air, other oxygen sources such as a process stream, or combinations thereof. The oxygen source may be gaseous or liquid. The stream of oxygen, for example dried air, may have less than about 1 ppm of water by weight therein. The amount of oxygen in the oxygen source may be controlled and/or selected to achieve a desired reaction conversion.

The invention also relates to system and or method to contact an ionic liquid catalyst with water to increase the activity of the ionic liquid catalyst within a production process. In an embodiment, an amount of water can be added to the ionic liquid catalyst to activate the catalyst and thereby increase the weight percent conversion of monomer feed, provided however that such amount of added water is less than an amount that undesirably deactivates the catalyst. The advantages of controlling water in a polyalphaolefin oligomerization reaction are described in detail in U.S. patent application Ser. No. 10/420,261, filed Apr. 22, 2003, and entitled "Method for Manufacturing High Viscosity Polyalphaolefins Using Ionic Liquid Catalysts" incorporated herein by reference in its entirety. In some embodiments, the ionic liquid and water are contacted prior to the reaction zone. In other embodiments, the ionic liquid and water are contacted in the reaction zone. In an embodiment of the present disclosure, both an amount of water as well as an amount of oxygen present in the reaction zone may be controlled to maintain the reaction and avoid deactivating the ionic liquid catalyst. Accordingly, disclosure regarding control of water in a reaction zone may be combined with control of oxygen as described herein. In an embodiment, the amount of water present in the reaction zone is from about 10 to about 20 ppm based upon the weight of the total reactants within the reaction zone. In an embodiment, the amount of water present in the reaction zone is controlled by a controller that is either the same or different than that of the oxygen controller 103 and is configured to control the amount of water such that the amount is less than an upper amount that is sufficient to deactivate the ionic liquid catalyst (e.g., formation of an undesirable amount of aluminum hydroxide from aluminum trichloride) and greater than a lower amount that is insufficient to maintain the desired reaction (e.g., conversion of monomer feed to less than about 20 weight percent) in the reaction zone.

The lower amount of water for a given ionic liquid catalyst composition may be determined experimentally by iteratively reducing the amount of water in the reaction zone and monitoring the monomer conversion until such conversion is unacceptable for the desired reaction. Conversely, the upper amount of water for a given ionic liquid catalyst composition may be determined experimentally by iteratively increasing the amount of water in the reaction zone and monitoring the catalyst deactivation until such deactivation is unacceptable for the desired reaction. What constitutes acceptable ionic liquid catalyst activity may depend upon, for example, the specific catalyst composition, the reaction conditions, and/or the types and properties (such as viscosity targets) for the end products being made. The routine experimentation required to determine the amount of oxygen required to achieve the effects described herein for a particular catalyst composition, the reaction conditions, and/or end product combination is within the ability of those skilled in the art in light of this disclosure.

In some embodiments, the maximum upper amount of water is the stoichiometric ratio of water that reacts with the catalyst to create a non-catalytic species thereof. For an ionic liquid catalyst comprising a chloroaluminate (e.g., $Al_2Cl_7^-$) that deactivates by reacting with water to form aluminum hydroxide, the maximum upper amount of water is a molar ratio of about 6 moles of water to each mole of chloroaluminate.

The amount of water present in the reaction zone may be controlled by controlling the amount of water in the monomer feed to the reaction zone, controlling the amount of water in a gas located in a headspace above the liquid components present in the reaction zone, or combinations thereof. The amount of water present in the ionic liquid catalyst, if any, is typically about constant and thus is not routinely adjusted or changed after initial control calibrations are performed.

In an embodiment, where the amount of water present in the monomer feed is controlled, the amount of water present in the feed is from about 1 to 100 ppm. In other embodiments where the amount of water is present in the monomer feed is controlled, the amount of water in the feed is from about 2 to about 60 ppm, alternatively, from about 3 to 30 ppm, alternatively, about 5 to about 15 ppm based upon the weight of the monomer feed. In an embodiment where the amount of water present in a headspace gas is controlled, the monomer feed is dried to a water content of less than. about 1 ppm by weight and an amount of wet gas such as moist nitrogen (e.g., nitrogen comprising an amount of water) is added to the reaction zone to control the amount of water therein. The moist nitrogen may be produced, for example, by bubbling dry nitrogen through water. In some embodiments, the amount of water present in the reaction zone is controlled to obtain a conversion of monomer feed to equal to or greater than about 20 weight percent. In other embodiments, the amount of water present in the reaction zone is controlled to obtain a conversion of monomer feed to equal to or greater than about 30, 40, 50, 60, 70, or 75 weight percent.

In an embodiment where the monomer feed is dried to less than about 1 ppm by weight and the headspace gas is dry nitrogen, the amount of water present in the reaction zone may be insufficient to maintain the desired reaction in the reaction zone, that is the conversion of the monomer feed was less than about 20 weight percent. In such an embodiment, the weight percent conversion of monomer feed can be increased by a) increasing the amount of water present in the reaction zone as discussed previously, for example by adding moist nitrogen to the reaction zone headspace or by other methods as known to those skilled in the art; b) adding oxygen to the reaction zone as discussed previously, for example by adding oxygen to the reaction zone headspace; or c) combinations of a) and b). Stated alternatively, an amount of water, oxygen, or both can be added to the ionic liquid catalyst in a manner described previously to activate the catalyst and thereby increase the weight percent conversion of monomer feed, provided however that such amount of added water, oxygen, or both is less than an amount that undesirably deactivates the catalyst. In some embodiments, the amount of oxygen and water present in the reaction zone is controlled to obtain a conversion of monomer feed to equal to or greater than about 20 weight percent. In other embodiments, the amount of oxygen and water present in the reaction zone is controlled to obtain a conversion of monomer feed to equal to or greater than about 30, 40, 50, 60, 70, or 75 weight percent.

Without intending to be bound by theory, it is believed that the ionic liquid catalysts require the presence of a proton donor such as an acid, and that water present or formed in the reaction zone reacts with the catalyst (e.g., chloroaluminate) to form hydrogen chloride, which serves as a proton donor to the remaining catalyst. In an embodiment, an acid, for example hydrogen chloride or other acids such a Bronsted acid or a Lewis acid, is added directly to the ionic liquid catalyst. For example, hydrogen chloride may be added directly to the ionic liquid catalyst by bubbling hydrogen chloride gas through the ionic liquid catalyst or by any other methods as known to those skilled in the art.

In an embodiment, an amount of oxygen, an amount of water, or both can be added to the ionic liquid catalyst in a manner described above to activate the catalyst and thereby increase the weight percent conversion of monomer feed, provided however that such amount of added oxygen, added water, or both is less than an amount that undesirably deactivates the catalyst. In this embodiment, the monomer conversion is from about 44% to about 58%; alternatively, from about 44% to about 70%; alternatively, from about 44% to about 85%; and alternatively, from about 44% to about 100%.

The amount of emulsification applied to the ionic liquid reaction mixture may be controlled as disclosed in previously referenced U.S. patent application Ser. No. 10/978,792 filed concurrently herewith and entitled "Method and System to Add High Shear to Improve an Ionic Liquid Catalyzed Chemical Reaction" which claims the benefit of and priority to provisional U.S. Patent Application No. 60/516,501, filed Oct. 31, 2003.

The catalyst concentration in the reaction zone may be used to control certain desired physical properties of the polyalphaolefin product. In an embodiment, the weight percent of ionic liquid catalyst introduced into the reaction zone may be from about 0.1 to about 50 wt. % based on the weight of the feed to the reactor, alternatively from about 0.1 to about 25 wt. %, alternatively from about 0.1 to about 10 wt. %, alternatively from about 0.1 to about 5 wt. %, alternatively, from about 1 to about 3 wt. %, alternatively, from about 1.5 to about 2.5 wt. %, and alternatively from about 2.0 to about 2.5 wt. %.

In the manufacture of polyalphaolefins, the monomer feedstock that is introduced into the reaction zone of the process comprises at least one alpha olefin. In an embodiment, the monomer feed comprises, based on the weight of the monomer feed, at least about 50 weight percent alpha olefins, alternatively, at least about 60, 70, 80, 90, 95, or 99 weight percent alpha olefins. In an embodiment, the monomer feed consists essentially of alpha olefins, which should be understood to include commercially available alpha olefin products. The alpha olefins and combinations thereof, which are also known as 1-olefins or 1-alkenes, suitable for use as the monomer feed of the process can have from 4 to 20 carbon atoms and include, for example, 1-butene, 1-pentene, 1-hexene, 1-octene, 1-decene, 1-dodecene, 1-tetradecene and combinations thereof. In some embodiments, the monomer feed comprises 1-decene. In other embodiments the monomer feed comprises 1-dodecene. In other embodiments, the monomer feed consists essentially of 1-decene, 1-dodecene, or mixture thereof. The alpha olefins of the monomer feed may have from 4 to 20 carbon atoms, or mixtures thereof, alternatively from 6 to 18 carbon atoms, and alternatively from about 10 to about 12 carbon atoms.

The reactor effluent withdrawn from the reaction zone generally comprises polyalphaolefins and the ionic liquid catalyst. A variety of polyalphaolefins can be produced according to the present disclosure. Polyalphaolefins are synthetic hydrocarbon liquids manufactured from monomers. Polyalphaolefins have a complex branched structure with an olefin bond, i.e., carbon-carbon double bond, that may be located anywhere along the molecule due to isomerization by the catalyst. As used herein, the term "polyalphaolefins" includes an alpha olefin oligomerization product that is either a dimer, a trimer, a tetramer, higher oligomers, a polymer of an alpha olefin, or a mixture of any one or more thereof, each of which has certain desired physical properties and, in particular, having the desired high viscosity properties all of which are more fully described below. Thus, the polyalphaolefins can include dimers, trimers, tetramers, higher oligomers, polymers, or mixture of any one or more thereof of the alpha olefin contained in the monomer feed. Such dimers, trimers, tetramers, higher oligomers, polymers, or mixture of any one or more thereof may comprise molecules having from 12 to over 1300 carbon atoms.

The reactor effluent can further comprise a dimer of the alpha olefin in the monomer feed and the unreacted monomer, if any. The polyalphaolefins can be separated from the other components of the reactor effluent including the ionic liquid catalyst, and, optionally, the unreacted monomer and dimers formed during the reaction of the monomer feed. The separated polyalphaolefins may undergo subsequent processing or upgrading such as hydrogenation to form a more stable polyalphaolefin product (referred to herein as a hydrogenated polyalphaolefin product), for example useful as a base oil stock. Hydrogenated polyalphaolefin products have olefin-carbons saturated with hydrogen, which lends excellent thermal stability to the molecule.

In an embodiment, the hydrogenated polyalphaolefin product has a viscosity of from about 2 to about 100 cSt@100° C., e.g., a low viscosity hydrogenated polyalphaolefin product having a viscosity of from about 2 to about 12 cSt@100° C., a medium viscosity hydrogenated polyalphaolefin product having a viscosity of from about 12 to about 40 cSt@100° C., or a high viscosity hydrogenated polyalphaolefin product having a viscosity of from about 40 to about 100 cSt@100° C. The weight average molecular weight of a hydrogenated polyalphaolefin product can be in the range of from about 170 to about 18,200, alternatively, from about 200 to about 10,000, alternatively from about 210 to about 8,000, alternatively from about 250 to about 3,000. In other embodiments, the weight average molecular weight of a hydrogenated polyalphaolefin product can be in the range of from about 500 to about 8,000; alternatively, from about 1,000 to about 5,000; and alternatively, from about 1,500 to 2,500.

In an embodiment, a hydrogenated polyalphaolefin product may be manufactured from either a 1-decene or 1-dodecene feedstock or mixtures thereof. The hydrogenated polyalphaolefin products from these feedstocks are especially significant in that they have unique physical properties. Typical ranges for the various physical properties of a hydrogenated polyalphaolefin product and the relevant test methods for determining the physical properties are presented in the following Table 1.

TABLE 1

Hydrogenated PAO Product Physical Properties

| Test | Units | Test Method | | Value |
|---|---|---|---|---|
| Kinematic Viscosity at 100° C. | cSt | ASTM D445 | Min | 12.0 |
| | | | Max | 35.0 |
| Bromine Index | mg/100 g | ASTM D2710 | Max | 800 |
| Volatility, Noack | wt % | CEC L40 T87 | Max | 2.0 |
| Flash Point | ° C. | ASTM D92 | Min | 245 |
| Fire Point | ° C. | ASTM D92 | Min | 290 |
| Pour Point | ° C. | ASTM D97 | Max | −30 |
| Polydispersity Index | | | Max | 3.5 |
| | | | Min | 1.0 |
| Weight Average Molecular Weight | | | Min | 170 |
| | | | Max | 18200 |

Any ionic liquid catalyst suitable to catalyze a desired chemical reaction may be used. Examples of ionic liquid compositions suitable for use in the inventive process are complexes of two components that form compositions that are liquid under the reaction conditions of the inventive process. Specifically, the ionic liquid catalyst is the complex resulting from the combination of a metal halide and an alkyl-containing amine hydrohalide salt. Such compositions are described in detail in U.S. Pat. Nos. 5,731,101 and 6,395,948, the disclosure of each of which is incorporated herein by reference in its entirety. It has been found that the use of such ionic liquid compositions provide for a polyalphaolefin end-products having certain desirable and novel physical properties that make them especially useful in various lubricant or lubricant additive applications. The use of an ionic liquid composition to produce a polyalphaolefin product is described in U.S. Pat. No. 6,395,948 and U.S. patent application Ser. No. 10/900221, filed Jun. 27, 2004, the disclosure of each of which is incorporated herein by reference in its entirety.

The metal halides that can be used to form the ionic liquid catalyst used in this invention are those compounds which can form ionic liquid complexes that are in liquid form at the reaction temperatures noted above when combined with an alkyl-containing amine hydrohalide salt. Examples of suitable metal halides are covalently bonded metal halides. Possible suitable metals which can be selected for use herein include those from Groups IVB, VIII, IB, IIB, and IIIA of the Periodic Table of the Elements, CAS version. More specifically, the metal of the metal halides can be selected from the group consisting of aluminum, gallium, iron, copper, zinc, titanium, and indium, alternatively from the group consisting of aluminum and gallium, and alternatively aluminum. Examples of metal halides include those selected from the group consisting of aluminum halide, alkyl aluminum halide, gallium halide, alkyl gallium halide, titanium halide, and alkyl titanium halide of which especially desired are aluminum halide or alkyl aluminum halide. In an embodiment, the metal halide is an aluminum halide or alkyl aluminum halide. In an embodiment, the metal halide is aluminum trichloride.

The alkyl-containing amine hydrohalide salts that can be used to form the ionic liquid catalyst used in this invention include monoamines, diamines, triamines and cyclic amines, all of which include one or more alkyl group and a hydrohalide anion. The term alkyl is intended to cover straight and branched alkyl groups having from 1 to 9 carbon atoms. Examples of alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. Examples of suitable compounds are those having the generic formula $R_3N$—$HX$, where at least one of the "R" groups is alkyl, for example an alkyl of from one to eight carbon atoms (for example, lower alkyl of from one to four carbon atoms) and X is halogen, for example chloride. If each of the three R groups is designated $R_1$, $R_2$ and $R_3$, respectively, the following possibilities exist in certain embodiments: each of $R_1$-$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. In an embodiment, these groups are methyl or ethyl groups. In an embodiment, the di- and tri-alkyl species can be used. In an embodiment, one or two of the R groups can be aryl. The alkyl groups, and aryl, if present, can be substituted with other groups, such as a halogen. Phenyl and benzyl are representative examples of possible aryl groups to select. However, such further substitution may undesirably increase the viscosity of the melt. Therefore, in an embodiment, the alkyl groups, and aryl, if present, are comprised of carbon and hydrogen groups, exclusively. Such short chains are desired because they form the least viscous or the most conductive melts. Mixtures of these alkyl-containing amine hydrohalide salts can be used.

Examples of amine hydrohalide salt are those compounds where the R groups are either hydrogen or an alkyl group having 1 to 4 carbon atoms, and the hydrohalide is hydrogen chloride, an example of which is trimethylamine hydrochloride.

The prepared the ionic liquid may be stored and subsequently used as a catalyst for the reactions described herein. Once used as a catalyst, the ionic liquid may be separated and/or recovered from the reaction effluent by methods known to those skilled in the art. The separated and/or recovered ionic liquid may be recycled as use as a catalyst either alone or in combination with freshly prepared ionic liquid catalyst. In some cases, the recycled ionic liquid composition may be refortified with a quantity of metal halide, or amine hydrohalide salt.

The following description incorporates the inventive process disclosed into an embodiment shown in FIG. 1 wherein is represented the production process 1 for manufacturing a hydrogenated polyalphaolefin product. Oxygen is injected into line 14 via line 101, the amount of which is controlled via controller 103. Monomer feed and the recycled monomer and dimer, which is more fully described below, are introduced or charged to reactor 10, hereinafter referred to as continuous stirred tank reaction or CSTR 10, by way of line 12. Makeup ionic liquid catalyst and recycled ionic liquid catalyst feed, which is more fully described below, are introduced or charged to CSTR 10 by way of line 14. The monomer and ionic liquid catalyst feeds are simultaneously introduced into the CSTR 10 while the reactor effluent from CSTR 10 is simultaneously with the introduction of the feeds withdrawn from CSTR 10 through line 16.

The reactor effluent is passed from CSTR 10 through line 16 to first phase separator 18 which provides means for separating the reactor effluent into an ionic liquid catalyst phase 20 and a hydrocarbon or polyalphaolefin-containing phase 22. The separated ionic liquid catalyst phase 20 is recycled by way of line 24 and combined with the makeup ionic liquid catalyst passing through line 14 and thereby is introduced into CSTR 10. The first phase separator may be any phase separator known to those skilled in the art to be able to separate two immiscible liquids having different densities. For example, the first phase separator may be a gravity separator or a centrifugal separator.

The polyalphaolefin-containing phase 22 passes from phase separator 18 through line 26 to deactivation vessel 28 which provides means for contacting any remaining ionic liquid catalyst mixed with the polyalphaolefin-containing phase with water so as to deactivate the ionic liquid catalyst. The mixture of polyalphaolefin-containing phase, water and deactivated ionic liquid catalyst passes from deactivation vessel 28 through line 30 to second phase separator 32 which provides means for separating the waste water and catalyst phases 34 and polyalphaolefin containing phase 36. The waste water phase passes from second phase separator 32 by way of line 37.

The polyalphaolefin-containing phase 36 passes from second phase separator 32 through line 38 to water wash vessel 40 which provides means for contacting the polyalphaolefin-containing phase 36 with fresh water. The fresh water is charged to or introduced into water wash vessel 40 through line 42. The water and polyalphaolefin-containing phases pass from water wash vessel 40 through line 44 to third phase separator 46 which provides means for separating the water and the polyalphaolefin-containing phase introduced therein from water wash vessel 40 into a water phase 48 and polyalphaolefin-containing phase 50. The water phase 48 can be recycled and introduced into deactivation vessel 28 through line 52 thereby providing the deactivation wash water for use in the deactivation vessel 28.

The polyalphaolefin-containing phase 50 passes from third phase separator 46 through line 54 to water separation vessel 56, which provides means for separating water from the polyalphaolefin-containing phase 50, for example by flash separation, to provide a flash water stream and a polyalphaolefin-containing phase having a low water concentration. The flash water stream can pass from water separation vessel 56 and recycled to deactivation vessel 28 through line 58, or alternatively, the flash water stream can be disposed of as waste water via line 37. The polyalphaolefin-containing phase having a low water concentration passes from water separation vessel 56 through line 60 and is charged to separation vessel 62, which is for example an evaporator. Separation vessel 62 provides means for separating the polyalphaolefin-containing phase having a low water concentration into a first stream comprising monomer and, optionally, dimer, and a second stream comprising a polyalphaolefin product. The first stream passes from separation vessel 62 by way of line 63 and is recycled to line 12 wherein it is mixed with the monomer feed and charged to CSTR 10.

The second stream passes from separation vessel 62 through line 64 to guard vessel 66, which defines a zone containing guard bed material and provides means for removing chlorine and other possible contaminants from the second stream prior to charging it to hydrogenation reactor 68. The effluent from guard vessel 66 passes through line 70 to hydrogenation reactor 68. Hydrogenation reactor 68 provides means for reacting the polyalphaolefin product in the second stream to provide a hydrogenated polyalphaolefin product of which a substantial portion of the carbon-carbon double bonds are saturated with hydrogen. Hydrogen is introduced by way of line 72 into line 70 and mixed with the second stream prior to charging the thus-mixed hydrogen and second stream into hydrogenation reactor 68. The hydrogenated polyalphaolefin product passes from hydrogenation reactor 68 by way of line 74.

The following examples of the invention are presented merely for the purpose of illustration and are not intended to limit in any manner the scope of the invention.

EXAMPLES 1-4

Controlling Oxygen in Oligomerization of 1-Decene

The following examples, examples 1-4, illustrate the effect of oxygen concentration in the headspace in the presence of a constant 10-15 ppm water in the feed on some of the physical properties of the oligomer reaction product and the percentage of monomer converted in the reaction resulting from the continuous process for the oligomerization of 1-decene.

Example 1

In a continuous process, 1-decene was fed at a rate of 2800 to 2900 grams/hour along with a catalyst feed (1.65:1 molar ratio $AlCl_3$:TMA.HCl) of 73 grams/hour into a 1-gallon stirred-tank reactor. The reactor was equipped with external and internal cooling coils. The 1-decene feed contained 10 to 15 ppm water. The reactor level was controlled to roughly half of the volume, which gave residence times from 22 to 37 minutes. A pump-around loop consisting of a high shear mixer and gear pump was used to ensure adequate contact between 1-decene and catalyst. The reactor stirrer was set at 660 rpm. The reaction section was controlled from 15 to 20° C. under a headspace of 21% oxygen (balance nitrogen) at a pressure of 30 psig. The reactor effluent was quenched with water to deactivate the catalyst. The resulting product was distilled targeting less than 2 weight percent monomer and dimer. Monomer conversion of the water-quenched product was determined using gas chromatography. The oligomer distribution, weight-averaged molecular weight (Mw) and polydispersity (D) of the distilled product were determined using gel permeation chromatography (GPC). The percent monomer conversion of the water-quenched product and the properties of the distilled product from this example and of the following examples are presented in Table 2 below.

TABLE 2

| | Units | Example 1 | Example 2 | Example 3 | Example 4 | Example 5 | Example 6 | Example 7 | Example 8 |
|---|---|---|---|---|---|---|---|---|---|
| Oxygen | % | 21 | 4.5 | 1 | 0 | 21 | 0 | 21 | 0 |
| Water | ppm | 10-15 | 10-15 | 10-15 | 10-15 | 0-1 | 65 | 52 | 0-1 |
| Monomer Conversion (before distillation) | % | 77 | 61 | 58 | 40 | 75 | 67 | 78 | 26 |
| Monomer | Weight % | 2.5 | <0.5 | 0.6 | 2.1 | 0 | 0.1 | 0 | 0.2 |
| Dimer | Weight % | 1.1 | 1.0 | 1.1 | 1.5 | 1.0 | 1.3 | 0.6 | 2.4 |
| Trimer | Weight % | 2.3 | 3.5 | 4.4 | 4.4 | 2.3 | 3.2 | 1.9 | 6.0 |
| Tetramer | Weight % | 2.8 | 4.1 | 5.2 | 5.2 | 2.8 | 3.9 | 2.5 | 6.8 |
| Pentamer | Weight % | 4.2 | 6.5 | 8.0 | 7.8 | 4.2 | 6.1 | 4.2 | 9.6 |
| Hexamer | Weight % | 5.0 | 7.4 | 8.5 | 8.6 | 5.0 | 7.0 | 5.1 | 10.0 |
| Heptamer + | Weight % | 82.1 | 77.6 | 72.1 | 70.4 | 84.7 | 78.4 | 85.7 | 64.9 |
| Mw | | 1717 | 1513 | 1369 | 1339 | 1778 | 1525 | 1759 | 1221 |
| D | | 1.57 | 1.31 | 1.34 | 1.44 | 1.37 | 1.33 | 1.29 | 1.33 |
| 100° C. Viscosity | cSt | 27.6 | 22.6 | 20.0 | 17.3 | 30.1 | 23.6 | 33.1 | 16.4 |
| 40° C. Viscosity | cSt | 217 | 175 | 150 | 126 | 255 | 194 | 234 | 120 |
| Viscosity Index | | 163 | 155 | 154 | 151 | 158 | 149 | 187 | 147 |
| Pour Point | ° C. | -46 | -46 | -49 | -51 | -48 | -45 | -40 | -48 |

Example 2

The conditions for Example 1 were repeated with the exception of the concentration of the oxygen in the headspace gas, which was 4.5% (balance nitrogen). The properties of the product obtained in this example are presented in Table 2. This example demonstrates that 4.5% oxygen in the reaction headspace results in higher monomer conversion and higher product viscosity compared to a reaction under nitrogen alone (see Example 4). The percent monomer conversion and product viscosity is lower than that observed under higher concentrations of oxygen in the headspace (see Example 1).

Example 3

The conditions for Example 1 were repeated with the exception of the concentration of the oxygen in the headspace gas, which was 1.0% (balance nitrogen) and that the headspace gas was swept through the reactor at a constant rate. The properties of the product obtained in this example are presented in Table 2. This example demonstrates that 1.0% oxygen in the reaction headspace results in higher monomer conversion and higher product viscosity compared to a reaction under nitrogen alone (see Example 4). The resulting monomer conversion and product viscosity is lower than that observed at an increased percentage of oxygen in the headspace (see Examples 1 and 2).

Example 4

The conditions for Example 1 were repeated with the exception of the composition of the headspace gas, which was nitrogen. The properties of the product obtained in this example are presented in Table 2. Comparison of the percent monomer conversion and product properties of the products described in Examples 1 and 4 demonstrate that a significant increase in percent monomer conversion and product viscosity can be realized with the control of oxygen in the reactor headspace.

EXAMPLES 5-7

Controlling Oxygen and/or Water in Oligomerization of 1-Decene

The following examples, examples 5-7, illustrate the effect of oxygen concentration and various amounts of water in the feed on some of the physical properties of the oligomer reaction product and the percentage of monomer converted in the reaction resulting from the continuous process for the oligomerization of 1-decene.

Example 5

The conditions for Example 1 were repeated with the exception of the water contained in the 1-decene feed, which was at 0-1 ppm. The properties of the product obtained in this example are presented in Table 2. Comparison of the percent monomer conversion and product properties of the products described in Examples 1 and 5 demonstrate that a significant increase in percent monomer conversion and product viscosity can be realized with the control of oxygen in the reactor headspace with or without the presence of water.

Example 6

The conditions for Example 1 were repeated with the exception of the composition of the headspace gas, which was nitrogen, and the water content in the 1-decene feed, which was 65 ppm. The properties of the product obtained in this example are presented in Table 2. Comparison of the percent monomer conversion and product properties of the products described in Examples 1 and 6 demonstrate in the absence of oxygen, but in the presence of water above 30 ppm, the 1-decene conversion approaches that achieved in the presence of oxygen.

Example 7

The conditions for Example 1 were repeated with the exception of the water content in the 1-decene feed, which was 52 ppm. The properties of the product obtained in this example are presented in Table 2. Comparison of the percent monomer conversion and product properties of the products described in Examples 1 and 7 demonstrate that in the presence of oxygen and greater than 30 ppm water, an increase in product viscosity is achieved.

Comparative Example 8

The conditions for Example 1 were repeated with the following exceptions: the 1-decene feed was passed through a molecular sieve desiccant bed to remove water from the feedstream, and the composition of the headspace gas was 100 percent nitrogen. The properties of the resulting product obtained in this example are presented in Table 2. Comparison of the percent monomer conversion and product properties for Example 8 to the products described in Examples 1 through 7 demonstrates that in the presence of oxygen or water, an increase in monomer conversion and product viscosity is achieved.

Ionic liquid catalysts are commonly used in processes such as the oligomerization of alpha olefins or the general oligomerization of olefins. Typically, in a catalytic reaction it is desirable to keep oxygen (or air) and water from entering the reaction zone because water or oxygen can deactivate the catalyst. However, in the method and system disclosed, the presence of oxygen and/or water increases an ionic liquid catalyst's activity resulting in increased monomer conversion in a PAO production process.

In the description above, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. There are shown in the drawings, and herein are described in detail, specific embodiments of the present invention with the understanding that the present disclosure is to be considered an exemplification of the principles of the invention, and is not intended to limit the invention to that illustrated and described herein. It is to be fully recognized that the different teachings of the embodiments discussed above may be employed separately or in any suitable combination to produce desired results. Specifically, the method and system of the present invention disclosed herein to contact an ionic liquid catalyst with oxygen may be used with any suitable ionic liquid catalyzed reaction wherein the reaction product contains a converted chemical reactant. In an embodiment, the method and system to contact an ionic liquid catalyst with oxygen of the present invention is for an oligomerization reaction for producing PAO from monomer in the presence of an ionic liquid based catalyst system and the detailed description above is focused on this embodiment but with the understanding that the present invention may have broader applications including the general oligomerization of olefins. Although only a few embodiments of the present invention have been described herein, it should be understood that the present invention may be embodied in many other specific forms without departing from the spirit or the scope of the present invention. Any examples included are to be considered as illustrative and not restrictive, and the invention is not to be limited to the details given herein, but may be modified within the scope of the appended claims along with their full scope of equivalents.

That which is claimed is:

1. A method to increase the activity of an ionic liquid catalyst comprising contacting an ionic liquid catalyst with molecular oxygen, wherein the contacting occurs prior to or within a reaction zone, wherein a reaction within the reaction zone is a polymerization reaction or an oligomerization reaction.

2. The method of claim 1 wherein the reaction within the reaction zone is the polymerization reaction.

3. The method of claim 1 wherein the reaction within the reaction zone is the oligomerization reaction.

4. The method of claim 3 further comprising feeding monomer and ionic liquid catalyst into the reaction zone.

5. The method of claim 4 wherein the monomer comprises alpha olefins having from about 4 to about 20 carbon atoms or mixtures thereof.

6. The method of claim 4 wherein the monomer comprises alpha olefins having from about 10 to about 12 carbon atoms or mixtures thereof.

7. The method of claim 4 wherein the oxygen is added to an ionic liquid catalyst feed.

8. The method of claim 4 wherein the oxygen is added to a monomer feed.

9. The method of claim 4 wherein the oxygen is added to a combined monomer and ionic liquid catalyst feed.

10. The method of claim 4 wherein the oxygen is added into a headspace of the reaction zone.

11. The method of claim 4 wherein the oxygen is added by bubbling oxygen up through the reaction zone.

12. The method of claim 1 further comprising controlling an amount of oxygen present in the reaction zone to maintain a desired reaction conversion.

13. The method of claim 12 wherein the amount of oxygen is controlled by controlling the amount of oxygen in a monomer feed to the reaction zone, controlling the amount of oxygen in an ionic liquid catalyst feed to the reaction zone, controlling the amount of oxygen in a combined monomer and ionic liquid catalyst feed to the reaction zone, controlling the amount of oxygen in a gas located in a headspace of the reaction zone, or a combination thereof.

14. The method of claim 12 further comprising controlling an amount of water present in the reaction zone to maintain a desired reaction conversion and avoid deactivating the catalyst.

15. The method of claim 14 wherein the amount of water is controlled by controlling the amount of water in a monomer feed to the reaction zone, controlling the amount of water in an ionic liquid catalyst feed to the reaction zone, controlling the amount of water in a combined monomer and ionic liquid catalyst feed to the reaction zone, controlling the amount of water in a gas located in a headspace of the reaction zone, or a combination thereof.

16. The method of claim 12 wherein the amount of oxygen is controlled such that oxygen comprises from at least about 0.5 to about 21 wt. % of the gas in a headspace above the reaction zone.

17. The method of claim 14 wherein the amount of oxygen is controlled such that oxygen comprises from at least about 0.5 to about 21 wt. % of the gas in a headspace above the reaction zone and the amount of water is controlled such that water comprises from at least about 0 to about 100 ppm based upon the weight of the total reactants within the reaction zone.

18. The method of claim 4 further comprising recovering polyalphaolefins from the reaction zone.

19. The method of claim 18 wherein a monomer conversion is from about 44% to about 100%.

20. A method comprising introducing into a reaction zone a monomer feed and an ionic liquid catalyst and controlling an amount of oxygen present in the reaction zone to maintain a conversion reaction of the monomer.

21. The method of claim 20 wherein the amount of oxygen is controlled by controlling the amount of oxygen in the monomer feed to the reaction zone, controlling the amount of oxygen in the ionic liquid catalyst feed to the reaction zone, controlling the amount of oxygen in a combined monomer and ionic liquid catalyst feed to the reaction zone, controlling the amount of oxygen in a gas located in a headspace of the reaction zone, or a combination thereof.

22. The method of claim 20 further comprising controlling the amount of water present in the reaction zone to maintain the conversion reaction of the monomer and avoid deactivating the catalyst.

23. The method of claim 22 wherein the amount of water is controlled by controlling the amount of water in the monomer feed to the reaction zone, controlling the amount of water in the ionic liquid catalyst feed to the reaction zone, controlling the amount of water in a combined monomer and ionic liquid catalyst feed to the reaction zone, controlling the amount of water in a gas located in a headspace of the reaction zone, or a combination thereof.

24. The method of claim 23 wherein the monomer feed is dried to a water content of less than about 1 ppm by weight and the amount of oxygen or wet gas is added to the reaction zone.

25. The method of claim 24 wherein the wet gas is moist nitrogen.

26. A method for catalytically oligomerizing a monomer into polyalphaolefins in a reaction zone, comprising contacting an ionic liquid catalyst with molecular oxygen prior to or within the reaction zone.

27. The method of claim 26 wherein the oxygen is added to the ionic liquid catalyst feed to the reaction zone, to the monomer feed to the reaction zone, to a combined monomer and ionic liquid catalyst feed to the reaction zone, to a headspace of the reaction zone, by bubbling oxygen up through the reaction zone, or combinations thereof.

28. The method of claim 27 further comprising controlling an amount of oxygen present in the reaction zone to maintain a desired reaction conversion, wherein the amount of oxygen is controlled by controlling the amount of oxygen in the monomer feed to the reaction zone, controlling the amount of oxygen in the ionic liquid catalyst feed to the reaction zone, controlling the amount of oxygen in the combined monomer and ionic liquid catalyst feed to the reaction zone, controlling the amount of oxygen in a gas located in the headspace of the reaction zone, or a combination thereof.

29. The method of claim 28 further comprising controlling the amount of water present in the reaction zone to maintain the desired reaction conversion and avoid deactivating the catalyst, the amount of water is controlled by controlling the amount of water in the monomer feed to the reaction zone, controlling the amount of water in the ionic liquid catalyst feed to the reaction zone, controlling the amount of water in the combined monomer and ionic liquid catalyst feed to the reaction zone, controlling the amount of water in the gas located in the headspace of the reaction zone, or a combination thereof.

* * * * *